United States Patent [19]

Eby et al.

[11] 4,040,810

[45] Aug. 9, 1977

[54] APPARATUS AND METHOD FOR TREATING WASTE PRODUCTS

[75] Inventors: Harry J. Eby, Greenbelt; Neal O. Morgan, Silver Spring, both of Md.

[73] Assignee: The United States of America as represented by the Secretary of Agriculture, Washington, D.C.

[21] Appl. No.: 665,586

[22] Filed: Mar. 10, 1976

[51] Int. Cl.² .......................................... C05F 11/08
[52] U.S. Cl. .......................................... 71/9; 71/15; 71/21; 119/1
[58] Field of Search ...................... 71/9, 15, 21; 119/1

[56] References Cited

U.S. PATENT DOCUMENTS

| 3,676,074 | 7/1972 | Shibayama et al. | 71/21 X |
| 3,716,371 | 2/1973 | Calvert et al. | 71/21 X |

OTHER PUBLICATIONS

Miller, B. F., Biological Digestion of Manure by Diptera, C. A. vol. 72, 1970, p. 231 – from Feedstuffs, 41(51) p. 32 - 1969.

*Primary Examiner*—Frank A. Spear, Jr.
*Assistant Examiner*—Ferris H. Lander
*Attorney, Agent, or Firm*—M. Howard Silverstein; William E. Scott; David G. McConnell

[57] ABSTRACT

An apparatus and method for treating waste products having a bioreducing unit, means for scrubbing air and gases exhausted from the unit and for recovering by-products formed in the bioreduction step, and means for dehumidifying the scrubbed air. Fly larvae which hatch from eggs added to the waste product in the bioreducing unit aerate the waste product and thus accelerate the bioreduction and removal of moisture. The fly larvae and the bioreduced manure are then separated on a perforated screen belt by utilizing the negative reaction of the larvae to light.

1 Claim, 6 Drawing Figures

APPARATUS AND METHOD FOR TREATING WASTE PRODUCTS

This invention relates to an apparatus and system for treating waste products. More particularly it relates to a system for removing odor from manure and for reclaiming some of the waste products.

With the advent of highly effective, tailor-made fertilizers, animal waste products are no longer used to any great extent for this purpose. Consequently, disposal of these undesirable, noxious wastes is a serious problem in many parts of the world, especially with the current emphasis on pollution control and reduction of the amount of polluting materials in the atmosphere.

Therefore, it is an object of this invention to provide a system for bioreducing manure to remove the odor and dry the manure.

Another object of this invention is to recover some of the by-products contained in the gases formed during the bioreducing process.

A further object is to provide a system of bioreducing manure that utilizes a combination of the bacteria normally present in manure and fly larvae to effect odor removal and drying of the manure.

A still further object is to provide a means of recovering and collecting the fly larvae when the bioreduction is completed.

According to the present invention the above objects are accomplished by an odor removal and dehumidifying apparatus in which a bioreducing unit such as a cylindrically shaped drum or tank in combination with a hollow, non-weight bearing shaft, an air scrubber, a dehumidifier, and means for connecting the bioreducing unit to both the air scrubber and the dehumidifier is used to bioreduce manure and recover useful by-products formed during the bioreduction process. The non-weight bearing shaft, which is axially situated in relation to the bioreducing unit is sealed internally at its longitudinal center and perforated ventrally along that portion that is inside the unit for the purpose of introducing and removing air and is provided with angle irons spaced at predetermined intervals along its length. The bioreducing unit is provided with drive means and bearings for rotation about the shaft. A chain drive is used for the purposes of this invention; however, any convenient type of drive means capable of rotating the unit is applicable. In addition to an exhaust blower situated near the air outlet end of the shaft for removing air and gases from the unit and a blower near the air inlet end of the shaft for flowing fresh and scrubbed air into the unit, the apparatus is provided with means for scrubbing and dehumidifying the air and gases removed from the unit. The scrubbing means consists of two fiberglass filter elements in series; the first is acid washed, and the second is alkaline washed. The acid and alkaline wash solutions are pumped from resevoirs to the top of the filter elements and allowed to flow by gravity through the elements to the reservoir. A dehumidifier connected to the scrubbing means provides for removal of excess moisture from the scrubbed air. The dehumidified air is then recirculated into the unit and through the rest of the system. The apparatus is also provided with a heating device between the scrubber and the dehumidifier to prevent build-up of frost on the cooling coils of the dehumidifier. Operation of the heating device is automatic and is controlled by a sensing element.

The above described odor removal and dehumidifying apparatus is further combined with an apparatus for separating fly larvae from bioreduced manure which consists essentially of a perforated conveyor belt and means for separating and collecting the larvae and the bioreduced manure.

The apparatus and process of this invention is more fully described with reference to the drawings wherein.

Figure 1:
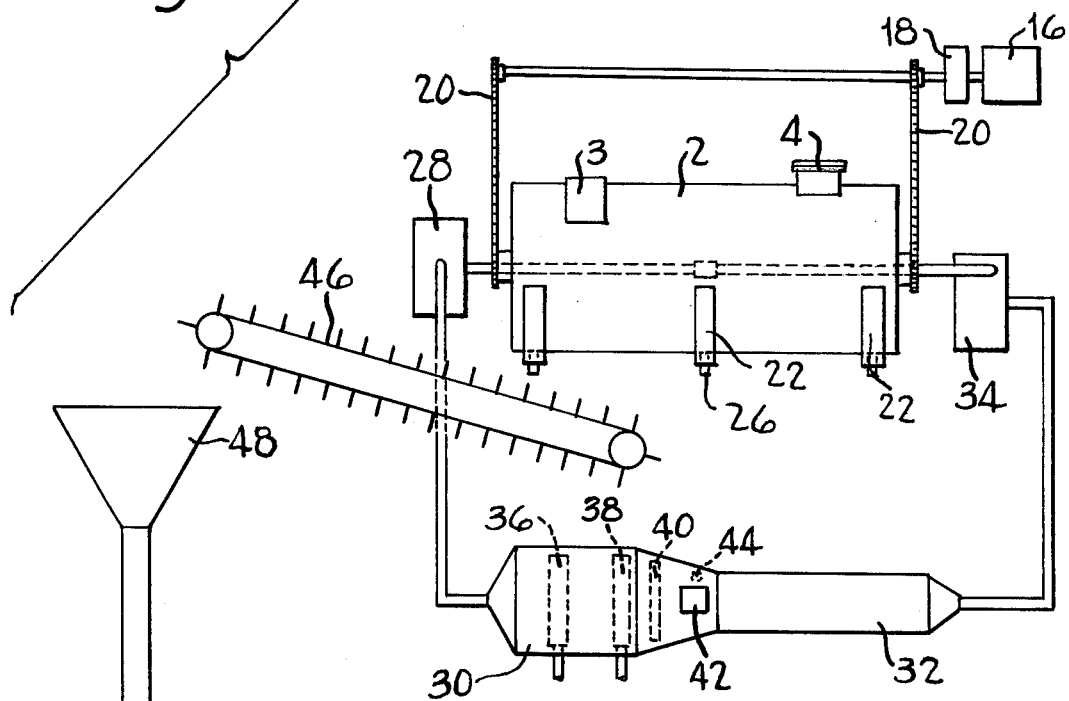
FIG. 1 is a schematic view of the complete apparatus.

In general, the apparatus of this invention is a combination of dynamic bioreducing unit which, for the purpose of this invention, is a cylindrically shaped drum 2, a hollow, non-weight bearing shaft 6, an air-scrubber 30, a dehumidifier 32, a perforated screen belt 50, and other means as shown in the figures that make the apparatus operational.

Figure 2:
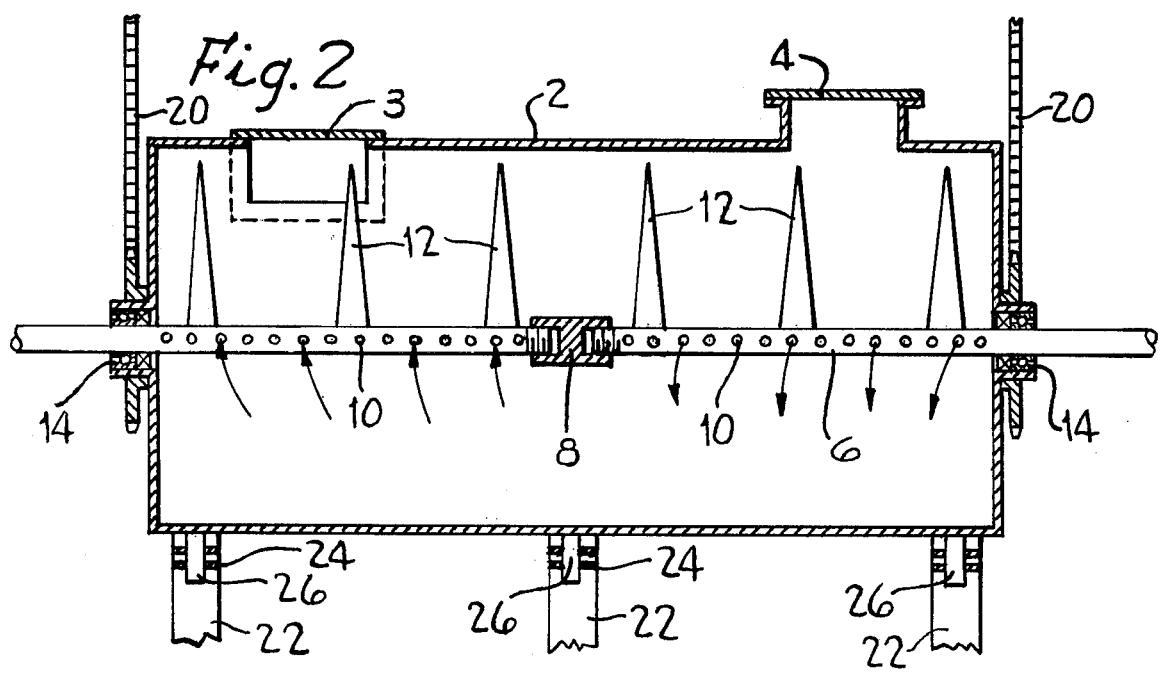
FIG. 2 is a view of the bioreducing unit partially in longitudinal cross section of the unit.
Figure 3:
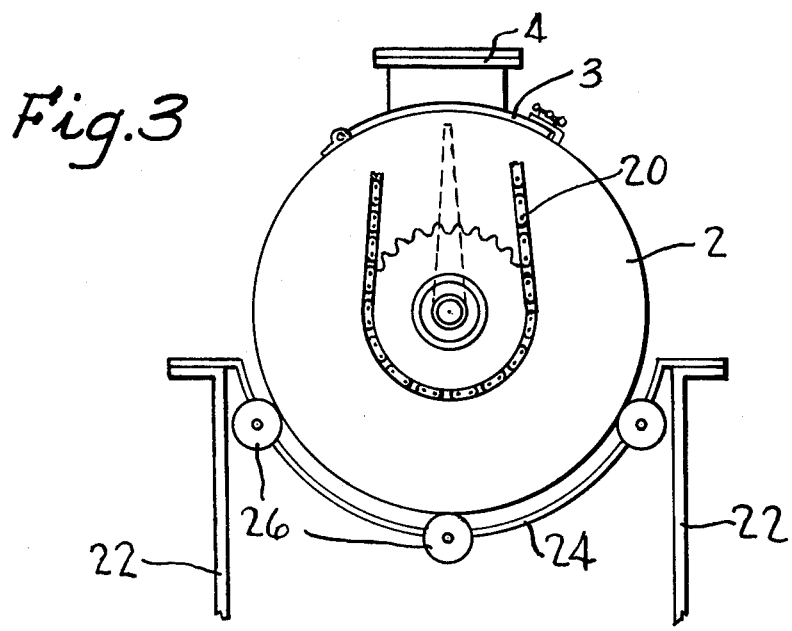
FIG. 3 is an end view of the bioreducing unit showing the chain drive and unit support.

Drum 2 is provided with doors 4 and 3 for loading and unloading purposes. Situated axially and running the length of drum 2 is hollow, non-weight bearing shaft 6 provided with internal seal 8 at its longitudinal center and with ventral perforations 10 for introduction of air and removal of air and biodegradation gases. Shaft 6 is also provided with angle irons 12, (FIG. 2) the apex of which point straight up, to aid in distributing the material being processed as drum 2 rotates. Bearings 14 are provided for drum 2 to rotate around shaft 6. Drive motor 16 and gear reducer 18 provide power for chain drives 20 to rotate drum 2. Drum supports 22 (FIGS. 2 & 3) are provided with straps 24 having roller bearings 26 for ease of drum rotation. Air and biodegradation gases are withdrawn from drum 2 through perforations 10 and hollow shaft 6 by exhaust blower 28. The withdrawn air and gases are blown through air scrubber 30 and dehumidifer 32 and are then recirculated to drum 2 through blower 34. Air scrubber 30 is equipped with air and scrubbing element 36 for removing ammonia, volatile solids, dust and gases other than $CO_2$ and an alkaline scrubbing element 38 for removing $CO_2$. Although not shown in the drawings both 36 and 38 are equipped with solution reservoirs and pumps for recirculating the acid solution through element 36 and the alkaline solution through element 38. Heating element 40 is provided to prevent frost build-up on the cooling coils in dehumidifier 32. Window 42 in conjunction with internal light 44 allows for observation of cooling coils which are defrosted automatically. Air volumn lost through removal of $CO_2$ is made up by the simple expedient of not making the sheet metal fitting on dehumidifier 32 air tight, thus allowing fresh air to be drawn into the system.

Figure 4:
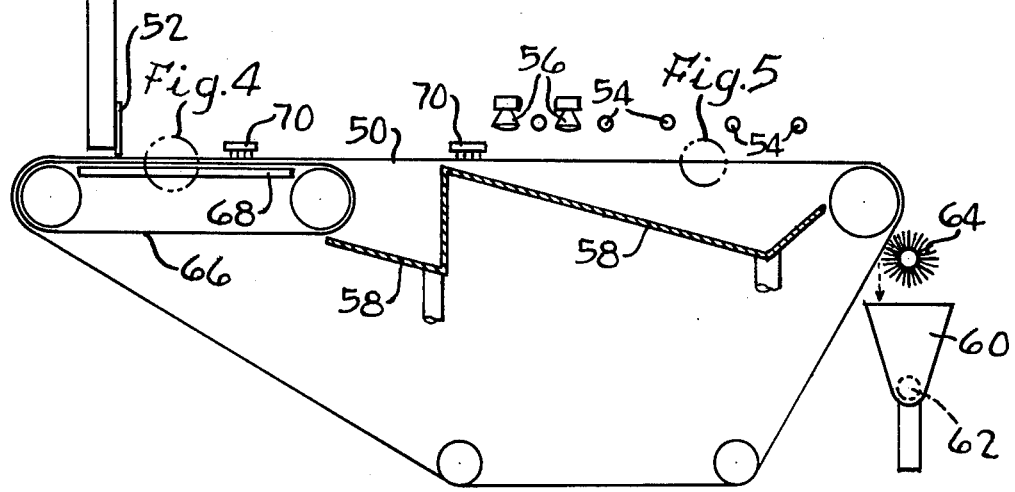
FIGS. 4 and 5 are exploded views of the sections of the perforated conveyor belt indicated in FIG. 1.
Figure 4:
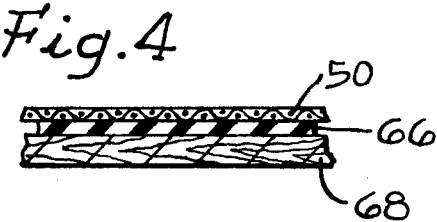
Figure 5:

When the manure has been dynamically bioreduced, the spent manure larvae mixture is emptied through drum unloading door 3 onto conveyor belt 46 which carries it to hopper 48 from which it is spread onto perforated screen belt 50, FIGS. 1 and 5. The depth of the layer that is spread onto 50 is kept to one-half inch or less by angle iron 52 at the bottom of hopper 48. Screen belt 50 carries the larvae and spent manure under a battery of fluorescent lights 54 where the larvae react negatively to the light and burrow through the manure and drop through the perforations into the collecting pans 58. Heat lamps 56 are also provided for use if needed. The spent manure is conveyed to hopper 60 which is provided with auger 62 for transferring the spent manure to a desired location of receptacle. Brush 64 is provided to remove any material stuck to belt 50. As shown in FIGS. 1 and 4, in order to prevent escape of larvae from belt 50 before they reach the area served by collecting trays 58, belt 50 rides on solid belt 66 provided for this purpose. Wooden deck 68 provides the rigidity necessary for leveling and adjusting the depth of the manure-larvae mixture. Steel fingers 70 are provided on vertically adjustable bars to level and spread the manure-larvae mix, keep the larvae active and exposed to light so they will burrow through and drop into collecting pans 58 and keep the manure from clumping. One of the pans 58 is placed to catch any larvae that goes through screen 50 before they reach the bank of lights 54 and 56. This prevents them from dropping onto the under side of the screen belt 50 and becoming smashed by the belt rollers and gumming up the belt.

In operation, drum 2 is loaded through door 4 with a waste product such as manure. Drum 2 is not limited in size and can be any convenient size depending on the magnitude of one's operation. For the purposes of this invention, drum 2 was large enough to conveniently hold and bioreduce 1.5 ton of manure. Fly eggs are added to the manure at the rate of 3 eggs per gram of manure. Circulation of air through shaft 6 is initiated and the mixture allowed to incubate for about 24 hours during which time larvae hatch out of the eggs. The manure is then dynamically bioreduced by rotating drum 2 for 5 days while air from shaft 6 is introduced to aerate the mixture and supply oxygen for the larvae and for the thermophilic bacteria naturally present in manure. The introduction of air in combination with the tumbling action of the rotating drum also provides cooling action and helps to maintain an optimum temperature of about 95° F in the mixture. It is noted that in the dynamic system provided by this invention the larvae burrow into the manure to a depth of at least a foot and a half whereas in a static system one would expect the larvae to burrow to a maximum depth of three inches. By burrowing deeper into the manure the larvae greatly accelerate aeration and release of moisture from the mass of manure thus demonstrating the advantages provided by the apparatus and process of this invention.

During the five days in which the manure is being tumbled by the rotation of drum 2 and redistributed by the action of angle irons 12, a number of gases such as hydrogen sulfide and ammonia are generated. Air and gases exhausted from drum 2 are scrubbed by elements 36 and 38 in scrubber 30 and some of the gases are converted to recoverable products. For instance, ammonia is converted to ammonia salts and carbon dioxide is removed as a calcium, barium or other insoluble carbonate and the converted products recovered.

Another by-product of the process is the larvae which are collected after being separated from the dry bioreduced manure. The larvae are dehydrated and granulated for use as a protein supplement to livestock feed.

We claim:

1. A process for treating manure, culturing fly larvae and recovering products formed during the treatment, comprising:

a. loading the manure into a rotatable bioreducing unit;

b. adding fly eggs to the manure in the unit;

c. aerating the manure-fly egg mixture in the unit;

d. allowing the fly eggs to hatch to the larval stage;

e. tumbling the manure-fly larvae mixture while circulating air through the unit to provide an environment for the larvae to burrow at least a foot and a half into the manure and for the manure to be dynamically bioreduced;

f. converting gases exhausted from the unit to salts and recovering the salts;

g. separating the bioreduced manure and fly larvae; and h. dehydrating and granulating the fly larvae.

* * * * *